United States Patent
Dai et al.

(10) Patent No.: US 12,371,394 B2
(45) Date of Patent: Jul. 29, 2025

(54) PLANT SQUALANE COMPOSITION, PREPARATION METHOD THEREOF, AND APPLICATION THEREOF

(71) Applicants: YICHUN DAHAIGUILIFE SCIENCE CO., LTD., Jiangxi (CN); WUHAN MINGMINGDE BIOCHEMISTRY CO., LTD., Hubei (CN)

(72) Inventors: Zhikai Dai, Jiangxi (CN); Haihui Sun, Jiangxi (CN); Huanhua Gan, Jiangxi (CN); Zhihua Xiong, Jiangxi (CN); Daoming Yi, Jiangxi (CN); Lerong Yi, Jiangxi (CN); Huiqi Huang, Jiangxi (CN); Bin Zhang, Jiangxi (CN)

(73) Assignees: YICHUN DAHAIGUILIFE SCIENCE CO., LTD., Yichun (CN); WUHAN MINGMINGDE BIOCHEMISTRY CO., LTD., Wuhan (CN)

( * ) Notice: Subject to any disclaimer, the term of this patent is extended or adjusted under 35 U.S.C. 154(b) by 0 days.

(21) Appl. No.: 18/874,570

(22) PCT Filed: Sep. 21, 2022

(86) PCT No.: PCT/CN2022/120323
§ 371 (c)(1),
(2) Date: Dec. 12, 2024

(87) PCT Pub. No.: WO2023/082849
PCT Pub. Date: May 19, 2023

(65) Prior Publication Data
US 2025/0214916 A1    Jul. 3, 2025

(30) Foreign Application Priority Data

Nov. 11, 2021   (CN) .......................... 202111334606.5

(51) Int. Cl.
C07C 5/03       (2006.01)
C07C 7/04       (2006.01)

(52) U.S. Cl.
CPC .................. *C07C 5/03* (2013.01); *C07C 7/04* (2013.01); *C07C 2523/755* (2013.01); *C07C 2525/02* (2013.01); *C07C 2601/08* (2017.05)

(58) Field of Classification Search
None
See application file for complete search history.

(56) References Cited

U.S. PATENT DOCUMENTS

| | | | | |
|---|---|---|---|---|
| 6,165,481 A | * | 12/2000 | Kaiya | A61K 39/39 424/401 |
| 9,545,440 B2 | * | 1/2017 | Hora | A61P 31/00 |
| 2015/0140030 A1 | * | 5/2015 | Looten | A61K 8/9711 424/195.17 |

FOREIGN PATENT DOCUMENTS

| CN | 112745186 A | 5/2021 |
|---|---|---|
| CN | 113956125 A | 1/2022 |
| JP | 2008013477 A | 1/2008 |

OTHER PUBLICATIONS

International Search Report issued in corresponding International application No. PCT/CN2022/120323, mailed Dec. 27, 2022.
Written Opinion of the International Search Authority in corresponding International application No. PCT/CN2022/120323, mailed Dec. 27, 2022.
Valerica Pandarus et al., "Solvent-Free Chemoselective Hydrogenation of Squalene to Squalane", ACS Omega, vol. 7, No. 2, issued on Jul. 26, 2017.
Notification to Grant Patent Right for Invention, Chinese Application No. 202111334606.5, mailed Sep. 15, 2022 (3 pages).
CNIPA, First Office Action issued for Chinese Application No. 202111334606.5, mailed May 7, 2022 (11 pages).
CNIPA, Reject decision issued for Chinese Application No. 202111334606.5, mailed Jun. 22, 2022 (10 pages).
CNIPA, Second Office Action issued for Chinese Application No. 202111334606.5, mailed Aug. 24, 2022 (7 pages).
Velerica Pandarus et al., "Solvent-free chemoselective hydrogenation of squalene to squalane", ACS Omega, vol. 2, No. 7, pp. 3989-3990 and 3991-3993, issued Jul. 26, 2017.

* cited by examiner

*Primary Examiner* — Ali Z Fadhel
(74) *Attorney, Agent, or Firm* — Daniel M. Cohn

(57) ABSTRACT

A plant squalane composition, a preparation method thereof, and an application thereof are provided. The plant squalane composition includes at least 92.0 wt % of squalane by weight and 0.5-3.0 wt % of cyclosqualane by weight. The preparation method includes hydrogenating a plant squalene raw material, separating the squalane and impurities in a crude plant squalane composition by fractionation, and refining the plant squalane composition. Squalene in the plant squalene raw material accounts for at least 70.0 wt % of a total weight of the plant squalene raw material. A content of the squalane in the plant squalane composition is not less than 92.0 wt %, and a content of the cyclosqualane in the plant squalane composition is 0.5-3.0 wt %. The preparation method solves problems of the prior art that an organic solvent is needed for catalytic hydrogenation, safety and environmental protection are poor, and excessive cyclosqualane is generated in a side reaction.

4 Claims, No Drawings

PLANT SQUALANE COMPOSITION, PREPARATION METHOD THEREOF, AND APPLICATION THEREOF

TECHNICAL FIELD

The present disclosure relates to a technical field of cosmetic raw materials, and in particular to a plant squalane composition, a preparation method thereof, and an application thereof.

BACKGROUND

Squalane, whose chemical name is 2, 6, 10, 15, 19, 23-hexamethyltetracosane, was first obtained by hydrogenating squalene extracted from livers of deep-sea fish (such as sharks). The squalane is a hydrocarbon oil with excellent performance, which is also known as deep-sea shark liver oil, is a rare animal oil with high chemical stability and excellent feel. Further, the squalane has good affinity to the skin, does not cause allergies and irritation, and is capable of accelerating a penetration of other active ingredients in cosmetics into the skin. Moreover, the squalane has low polarity and medium spreadability and is pure, colorless, and odorless, so the squalane is mainly used in the cosmetics industry.

Animal squalene is mainly derived from the deep-sea shark liver oil. Among different types of deep-sea shark liver oils, the squalene has a high content (15% to 80%) in a shark liver, has few impurities, and is simple to extract. After extraction, a squalene containing the squalene with a content of up to 99% is obtained. However, considering increasing depletion of marine shark resources, a low reproduction rate of wild sharks, and a pollution of fish species caused by environmental damage, as well as a protection of wild marine animals, countries around the world have included the wild sharks in a scope of protected animals, and the countries strictly prohibited killing of the wild sharks to prevent the depletion of the wild sharks. Therefore, people can hardly obtain animal squalene by killing the wild sharks. Thus, it is particularly urgent to find other renewable resources to replace the animal squalene extracted from the wild sharks, and extracting the squalene from plants gradually becomes a research trend.

In recent years, research on extracting the squalene from plants has made rapid progress. The squalene is found in a variety of plants, especially oil plants. Specifically, the squalene is contained in vegetable oils such as olive oil, soybean oil, rapeseed oil, rice bran oil, and sunflower oil, and a content of the squalene is higher in the olive oil. Plant raw materials, especially a deodorized distillate of the vegetable oil (also known as DD oil), are a good source of the squalene. At present, the DD oil is mainly used in the field to extract the squalene, but the squalene can only be extracted from olive DD oil. In Europe, an extraction of the plant squalene from the olive DD oil has been realized in industrial production and is widely used in cosmetics industry. In addition, due to a low content of the squalene in other plant DD oils (the soybean oil, corn oil, palm oil, the rapeseed oil, and the sunflower oil, etc.), extraction difficulty is large and cost is high, and only a few companies have comprehensive extraction and utilization capabilities to extract the plant squalene.

As the name implies, the plant squalane is mainly made from the plant squalene through a hydrogenation process. In the current squalene hydrogenation technology, organic solvents are mainly used to achieve catalytic hydrogenation, which has poor safety, poor environmental protection, and high cost, and does not conform to a development trend of green chemistry. In addition, in the prior art, side reactions during the hydrogenation process may produce too much cyclosqualane. Moreover, when a content of the squalene in a raw material is low, hydrogenation is often incomplete, affecting quality of final obtained squalane, of which is disclosed in a non-patent literature [Pandarus V, Ciriminna R, Kaliaguine S, et al. Heterogeneously Catalyzed Hydrogenation of Squalene to Squalane under Mild Conditions [J]. ChemCatChem, 2015, 7 (14): 2071-2076.]. In a presence of a solvent and mild condition, when the content of the squalene in the raw material reaches 98%, the hydrogenation of the squalene is completed in 4 hours. Under the same condition, when the content of the squalene in the raw material is 92%, it takes 8 hours to complete the hydrogenation of the squalene. When using the plant squalene derived from olives (a content of the squalene thereof is 82%), the hydrogenation of the squalene thereof is incomplete. Even if a reaction time is extended to 24 hours, only 4 of 6 double bonds of the squalene are hydrogenated, and the rest are incompletely hydrogenated. In addition, even if high-content squalene raw material is used, noble metal Pd/C used is only allowed to be reused for five times, and a catalytic activity is obviously reduced when the noble metal Pd/C is reused for a sixth time. It is indicated that the content of the squalene in the raw material has a significant impact on hydrogenation.

Under solvent-free conditions, the catalyst is easily deactivated and the squalene is not easy to be fully hydrogenated, so the content of the squalene in the raw material is required to be high, which is disclosed in a non-patent literature [Pandarus V, Ciriminna R, Béland F, et al. Solvent-free chemoselective hydrogenation of squalene to squalane [J]. ACS Omega, 2017, 2 (7): 3989-3996.]. Specifically, under a solvent-free condition, an effect and number of repetitions of a palladium-carbon catalyst were investigated using olive squalene with a squalene content of 82% as the raw material. The literature has achieved a maximum of eight applications of the palladium-carbon catalyst, but for each of the 8 applications, the palladium-carbon catalyst needs to be washed with an organic solvent to remove surface grease after filtering. In addition, under the solvent-free condition, the olive squalene only takes 20 hours to reach equilibrium when the palladium-carbon catalyst is applied for the first to third time, and a hydrogenation reaction time of the olive squalene is significantly prolonged when the palladium-carbon catalyst is applied for the fourth to eighth time, and a longest time thereof is up to 40 hours. It is noted that an activity of the palladium-carbon catalyst decreases with each repeated use until the palladium-carbon catalyst is unable to be reused for the ninth time.

But surprisingly, under the solvent-free condition, a hydrogenation reaction rate is greatly accelerated by increasing a hydrogenation pressure and a temperature. At the same time, use of a cheap nickel catalyst also catalyzes the hydrogenation reaction of the squalene well, solving a problem of unstable activity of an expensive catalyst when being reused.

SUMMARY

In view of above situations, the present disclosure provides a plant squalane composition, a preparation method thereof, and an application thereof to solve problems in the prior art that organic solvents are needed for catalytic hydrogenation, poor catalytic stability of a repeatedly reused catalyst, poor safety and environmental protection, and high production costs.

The present disclosure provides a plant squalane composition. The plant squalane composition comprises at least 92.0 wt % of squalane by weight and 0.5-3.0 wt % of cyclosqualane by weight.

A chemical structure of the squalane is:

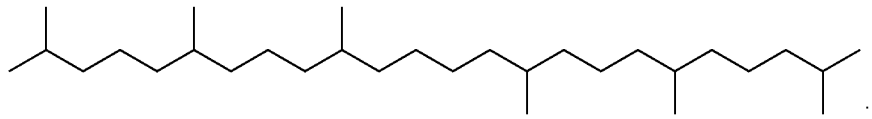 [SMILES: CC(C)CCCC(C)CCCC(C)CCCCC(C)CCCC(C)CCCC(C)C]

A chemical structure of the cyclosqualane is:

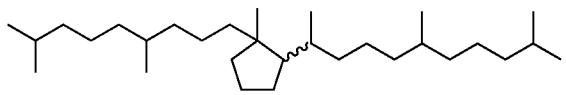 [SMILES: CC(C)CCCC(C)CCCC(C)C1CCCC1(C)CCCC(C)CCCC(C)C]

Optionally, an iodine value of the plant squalane composition is not greater than 4.0 g/100 g, a saponification value of the plant squalane composition is not greater than 3.0 mg KOH/g, an acid value of the plant squalane composition is not greater than 0.2 mg KOH/g, and a refractive index of the plant squalane composition is 1.450-1.460 (20° C.).

The present disclosure further provides a preparation method of the plant squalane composition. The preparation method comprises steps 1-3.

The step 1 comprises hydrogenating a plant squalene raw material. Squalene in the plant squalene raw material accounts for at least 70.0 wt % of a total weight of the plant squalene raw material.

The step 2 comprises separating the squalane and impurities by fractionation to obtain the plant squalane composition. A content of the squalane in the plant squalane composition is not less than 92.0 wt %, and a content of the cyclosqualane in the plant squalane composition is 0.5-3.0 wt %.

The step 3 comprises refining the plant squalane composition.

Optionally, in the step 1, a catalyst for hydrogenating the plant squalene raw material is metal nickel, supported nickel, or Raney nickel, a hydrogenation temperature is 180-220° C., and a hydrogenation pressure is 5-15 MPa, and a hydrogenation time is 6-24 hours.

During a hydrogenation process, part of the squalene is converted into the cyclosqualane, a ratio of the cyclosqualane to the squalane is 1-10%.

Optionally, the step 2 comprises steps 21-22.

The step 21 comprises performing a first distillation to remove plant alkane, fatty acid alkyl ester, and a small amount of the squalane, where removed plant alkane and removed fatty acid alkyl ester have a low boiling-point. First remaining material comprises most of the squalane, plant alkane, the cyclosqualane, and plant asphalt.

The step 22 comprises performing a second distillation to obtain a main composition containing the squalane and the cyclosqualane, and enabling that the content of the squalane in the main composition is not less than 92.0 wt % and the content of the cyclosqualane is 0.5-3.0 wt % by adjusting parameters. Second remaining material is the plant asphalt with a high-boiling point.

Optionally, the first distillation is carried out on a packed tower equivalent to 20 theoretical plates, under a system vacuum of 10-1000 Pa, with a bottom temperature of 200-230° C. and a top temperature of 170-190° C.

Optionally, the second distillation is carried out on a packed tower equivalent to 20 theoretical plates, under a system vacuum of 10-1000 Pa, with a bottom temperature of 220-250° C. and a top temperature of 180-200° C.

Optionally, in the step 3, a refining process comprises winterization, decolorization and deodorization, and a melting point of the plant squalane composition after the refining process is 0-5° C.

In the plant squalane composition and the preparation method of the present disclosure, the plant squalene raw material with the squalene of the content not less than 70.0 wt % is hydrogenated and refined. In the hydrogenation process, only a cheap nickel-based catalyst (i.e., the metallic nickel, the supported nickel, or the Raney nickel, a price of which is only 0.1%-5% of a palladium-carbon catalyst) needed, and no organic solvent needs to be added, which is environmentally friendly. At the same time, the cheap nickel-based catalyst is a disposable catalyst, and there is no need to consider reuse of the catalyst, which greatly reduces a difficulty of the hydrogenation of the squalene and improves stability of hydrogenation. In addition, although the cyclosqualane is produced by side reactions during the hydrogenation process, the present disclosure is able to partially remove the cyclosqualane by high vacuum distillation during the refining process, reduce the proportion of the cyclosqualane in the plant squalane composition, further enrich the squalane, and maintain the content of the cyclosqualane at 0.5-3.0 wt %, and improve the content and quality of the squalane.

In addition, the present disclosure further provides an application of the plant squalane composition. The plant squalane composition is applied in cosmetics.

DETAILED DESCRIPTION

For ease of understanding the present disclosure, the present disclosure is described fully hereinafter with reference to the accompanying drawings. Several embodiments of the present disclosure are given in the accompanying drawings. However, the present disclosure may be implemented in many different forms and is not limited to the embodiments described herein. On the contrary, a purpose of providing these embodiments is to make the disclosure of the present disclosure more thorough and comprehensive.

Unless otherwise defined, all technical and scientific terms used herein have the same meaning as commonly understood by those skilled in the art of the present disclosure. The terms used in the specification of the present disclosure are only for the purpose of describing specific embodiments, and are not intended to limit the present disclosure. As used herein, the term "and/or" includes all combinations including one or more of associated listed items.

Following methods are used to measure parameters of the plant squalane composition, a squalane content, an iodine value, an acid value, a saponification value, a relative density, and a refractive index.

Detection of a content of squalane and a content of cyclosqualane: the content of the squalane and the content of the cyclosqualane are detected by a Gas chromatography-mass spectrometry (GC-MS), where a molecular weight of the squalene is 410 (MV), a molecular weight of the squalane is 422 (MV), and a molecular weight of the cyclosqualane is 420 (MV).

The iodine value of the plant squalane composition is detected according to GB/T 5532-2008 Determination of iodine value of animal and vegetable fats and oils.

The acid value of the plant squalane composition is detected according to GB/T 5530-2005 Determination of acid value and acidity of animal and vegetable fats and oils.

The saponification value of the plant squalane composition is detected according to GB/T 5534-2008 Determination of saponification value of animal and vegetable fats and oils.

The refractive index of the plant squalane composition is detected according to GB/T 6488-2008 Determination of refractive index of liquid chemical products (20° C.).

Embodiment 1

The embodiment provides a preparation method of a plant squalane composition. The preparation method comprises steps 1-3.

The step 1 comprises hydrogenating a plant squalene raw material. Squalene in the plant squalene raw material accounts for 76.3 wt % of a total weight of the plant squalene raw material (remaining components in the plant squalene raw material are plant olefins, a plant wax and a small amount of fatty acid alkyl ester, where the plant olefins and the plant wax have the same boiling point, and the fatty acid alkyl ester have a higher boiling point than the plant olefins and the plant wax). A catalyst for hydrogenating the plant squalene raw material is a 3 wt % nickel-based catalyst (product name: Pricat9910, Johnson Matthey). After the plant squalene raw material and the catalyst are evenly mixed, the plant squalene raw material is hydrogenated at a hydrogenation temperature of 180° C. for 16 hours under a hydrogenation pressure of 8 MPa.

During a hydrogenation process, part of the squalene is converted into cyclosqualane. A conversion rate of the squalene is monitored by the GC-MS. A content of the squalane and a content of the cyclosqualane in a crude plant squalane composition obtained after the hydrogenation process are respectively 71.0 wt %, and 4.5 wt %, of a total weight of the crude plant squalane composition. A remaining material is a small amount of non-squalane alkane, wax, alkyl ester and pigments, etc., and a ratio of the cyclosqualane to the squalane is 6.34%.

The step 2 comprises separating the squalane and impurities in the crude plant squalane composition by fractionation. The step 2 specifically comprises steps 21 and 22.

The step 21 comprises performing a first distillation on the crude plant squalane composition obtained in the step 1. Specifically, the crude plant squalane composition is continuously introduced into a falling film distillation tower with 20 theoretical plates, and the crude plant squalane composition is continuously vaporized in a falling film evaporator of the falling film distillation tower, and is balance, and separated in a distillation tower of the falling film distillation tower. The first distillation is carried out under a vacuum of 50 Pa, a bottom temperature of 200° C., and a top temperature of 170° C. As a result, light components are continuously extracted, where the light components comprises non-squalane alkane, a small amount of the squalane and fatty acid alkyl ester.

The step 22 comprises performing a second distillation. A tower bottom material obtained after a first stage distillation is continuously introduced into the falling film distillation tower with 20 theoretical plates. The tower bottom material is continuously vaporized in the falling film evaporator, and the tower bottom material is allowed to balance and separate in the distillation tower. The second distillation is carried out under the vacuum of 50 Pa, the bottom temperature of 220° C., and the top temperature of 180° C. A main component containing the squalane is continuously extracted. The content of squalane in the main composition is detected to be 93.5 wt %, and the content of cyclosqualane is 1.8 wt %.

The step 3 comprises refining the plant squalane composition. A refining process comprises winterization, decolorization and deodorization.

A melting point of the plant squalane composition is measured to be 1.4° C., an iodine value of the plant squalane composition is 2.9 g/100 g, a saponification value of the plant squalane composition is 0.5 mg KOH/g, an acid value of the plant squalane composition is 0.15 mg KOH/g, and a refractive index of the plant squalane composition is 1.460 (20° C.).

The embodiment further provides an application of the plant squalane composition. The plant squalane composition is applied in cosmetics.

Embodiment 2

The embodiment provides a preparation method of a plant squalane composition. The preparation method comprises steps 1-3.

The step 1 comprises hydrogenating a plant squalene raw material. Squalene in the plant squalene raw material accounts for 73.5 wt % of a total weight of the plant squalene raw material (remaining components in the plant squalene raw material are plant olefins, a plant wax and a small amount of fatty acid alkyl ester, where the plant olefins and the plant wax have the same boiling point, and the fatty acid alkyl ester have a higher boiling point than the plant olefins and the plant wax). A catalyst for hydrogenating the plant squalene raw material is a 2 wt % supported nickel catalyst (product name: NiCAT-8800P, Shanghai Xunkai New Materials). After the plant squalene raw material and the catalyst are evenly mixed, the plant squalene raw material is hydrogenated at a hydrogenation temperature of 200° C. for 10 hours under a hydrogenation pressure of 10 MPa.

During a hydrogenation process, part of the squalene is converted into cyclosqualane. A conversion rate of the squalene is monitored by the GC-MS. A content of the squalane and a content of the cyclosqualane in a crude plant squalane composition obtained after the hydrogenation process are respectively 71.3 wt %, and 2.2 wt %, of a total weight of the crude plant squalane composition. A remaining material is a small amount of non-squalane alkane, a wax, alkyl ester, and pigments, etc., and a ratio of the cyclosqualane to the squalane is 3.09%.

The step 2 comprises separating the squalane and impurities in the crude plant squalane composition by fractionation. The step 2 specifically comprises steps 21 and 22.

The step 21 comprises performing a first distillation on the crude plant squalane composition obtained in the step 1. Specifically, the crude plant squalane composition is continuously introduced into a falling film distillation tower with 20 theoretical plates, and the crude plant squalane composition is continuously vaporized in a falling film evaporator of the falling film distillation tower, and is balance, and separated in a distillation tower of the falling film distillation tower. The first distillation is carried out under a vacuum of 100 Pa, a bottom temperature of 210° C., and a top temperature of 180° C. As a result, light components are continuously extracted, where the light components comprises non-squalane alkane, a small amount of the squalane and the fatty acid alkyl ester.

The step 22 comprises performing a second distillation. A tower bottom material obtained after a first stage distillation is continuously introduced into the falling film distillation tower with 20 theoretical plates. The tower bottom material is continuously vaporized in the falling film evaporator, and the tower bottom material is allowed to balance and separate in the distillation tower. The second distillation is carried out under the vacuum of 100 Pa, the bottom temperature of 220° C., and the top temperature of 180° C. A main component containing the squalane is continuously extracted. The content of squalane in the main composition is detected to be 93.8 wt %, and the content of cyclosqualane is 1.2 wt %.

The step 3 comprises refining the plant squalane composition. A refining process comprises winterization, decolorization and deodorization.

A melting point of the plant squalane composition finally obtained is measured to be 0.9° C., an iodine value of the plant squalane composition is 4 g/100 g, a saponification value of the plant squalane composition is 0.4 mg KOH/g, an acid value of the plant squalane composition is 0.17 mg KOH/g, and a refractive index of the plant squalane composition is 1.450 (20° C.).

The embodiment further provides an application of the plant squalane composition. The plant squalane composition is applied in cosmetics.

Embodiment 3

The embodiment provides a preparation method of a plant squalane composition. The preparation method comprises steps 1-3.

The step 1 comprises hydrogenating a plant squalene raw material. Squalene in the plant squalene raw material accounts for 91 wt % of a total weight of the plant squalene raw material (remaining components in the plant squalene raw material are plant olefins, a plant wax and a small amount of fatty acid alkyl ester, where the plant olefins and the plant wax have the same boiling point, and the fatty acid alkyl ester have a higher boiling point than the plant olefins and the plant wax). A catalyst for hydrogenating the plant squalene raw material is a 2 wt % nickel-based catalyst (product name: Nysofact, Engelhard Corporation) After the plant squalene raw material and the catalyst are evenly mixed, the plant squalene raw material is hydrogenated at a hydrogenation temperature of 190° C. for 12 hours under a hydrogenation pressure of 13 MPa.

During a hydrogenation process, part of the squalene is converted into cyclosqualane. A conversion rate of the squalene is monitored by the GC-MS. A content of the squalane and a content of the cyclosqualane in a crude plant squalane composition obtained after the hydrogenation process are respectively 90.0 wt %, and 0.9 wt %, of a total weight of the crude plant squalane composition. A remaining material is a small amount of non-squalane alkane, wax, alkyl ester, and pigments, etc., and a ratio of the cyclosqualane to the squalane is 1.00%.

The step 2 comprises separating the squalane and impurities in the crude plant squalane composition by fractionation. The step 2 specifically comprises steps 21 and 22.

The step 21 comprises performing a first distillation on the crude plant squalane composition obtained in the step 1. Specifically, the crude plant squalane composition is continuously introduced into a falling film distillation tower with 20 theoretical plates, and the crude plant squalane composition is continuously vaporized in a falling film evaporator of the falling film distillation tower, and is balance, and separated in a distillation tower of the falling film distillation tower. The first distillation is carried out under a vacuum of 300 Pa, a bottom temperature of 220° C., and a top temperature of 185° C. As a result, light components are continuously extracted, where the light components comprises non-squalane alkane, a small amount of the squalane and the fatty acid alkyl ester.

The step 22 comprises performing a second distillation. A tower bottom material obtained after a first stage distillation is continuously introduced into the falling film distillation tower with 20 theoretical plates. The tower bottom material is continuously vaporized in the falling film evaporator, and the tower bottom material is allowed to balance and separate in the distillation tower. The second distillation is carried out under the vacuum of 300 Pa, the bottom temperature of 240° C., and the top temperature of 195° C. A main component containing the squalane is continuously extracted. The content of squalane in the main composition is detected to be 96.8 wt %, and the content of cyclosqualane is 0.5 wt %.

The step 3 comprises refining the plant squalane composition. A refining process comprises winterization, decolorization and deodorization.

A melting point of the plant squalane composition finally obtained is measured to be 0° C., an iodine value of the plant squalane composition is 1.4 g/100 g, a saponification value of the plant squalane composition is 2.1 mg KOH/g, an acid value of the plant squalane composition is 0.15 mg KOH/g, and a refractive index of the plant squalane composition is 1.455 (20° C.).

The embodiment further provides an application of the plant squalane composition. The plant squalane composition is applied in cosmetics.

Embodiment 4

The embodiment provides a preparation method of a plant squalane composition. The preparation method comprises steps 1-3.

The step 1 comprises hydrogenating a plant squalene raw material. Squalene in the plant squalene raw material accounts for 85.2 wt % of a total weight of the plant squalene raw material (remaining components in the plant squalene raw material are plant olefins, a plant wax, and a small amount of fatty acid alkyl ester, where the plant olefins and the plant wax have the same boiling point, and the fatty acid alkyl ester have a higher boiling point than the plant olefins and the plant wax). A catalyst for hydrogenating the plant squalene raw material is a 5 wt % Raney nickel catalyst (product name: Raney nickel, Jiangsu Raney Metal Technology Co., Ltd). After the plant squalene raw material and the catalyst are evenly mixed, the plant squalene raw material is hydrogenated at a hydrogenation temperature of 210° C. for 9 hours under a hydrogenation pressure of 5 MPa.

During a hydrogenation process, part of the squalene is converted into cyclosqualane. A conversion rate of the squalene is monitored by the GC-MS. A content of the squalane and a content of the cyclosqualane in a crude plant squalane composition obtained after the hydrogenation process are respectively 75.6 wt %, and 7.5 wt %, of a total weight of the crude plant squalane composition. A remaining material is a small amount of non-squalane alkane, wax, alkyl ester, and pigments, etc., and a ratio of the cyclosqualane to the squalane is 9.92%.

The step 2 comprises separating the squalane and impurities in the crude plant squalane composition by fractionation. The step 2 specifically comprises steps 21 and 22.

The step 21 comprises performing a first distillation on the crude plant squalane composition obtained in the step 1. Specifically, the crude plant squalane composition is continuously introduced into a falling film distillation tower with 20 theoretical plates, and the crude plant squalane composition is continuously vaporized in a falling film evaporator of the falling film distillation tower, is balance, and separated in a distillation tower of the falling film distillation tower. The first distillation is carried out under a vacuum of 500 Pa, a bottom temperature of 230° C., and a top temperature of 190° C. As a result, light components are continuously extracted, where the light components comprises non-squalane alkane, a small amount of the squalane and the fatty acid alkyl ester.

The step 22 comprises performing a second distillation. A tower bottom material obtained after a first stage distillation is continuously introduced into the falling film distillation tower with 20 theoretical plates. The tower bottom material is continuously vaporized in the falling film evaporator, and the tower bottom material is allowed to balance and separate in the distillation tower. The second distillation is carried out under the vacuum of 500 Pa, the bottom temperature of 250° C., and the top temperature of 200° C. A main component containing the squalane is continuously extracted. The content of squalane in the main composition is detected to be 92.0 wt %, and the content of cyclosqualane is 3.0 wt %.

The step 3 comprises refining the plant squalane composition. A refining process comprises winterization, decolorization and deodorization.

A melting point of the plant squalane composition finally obtained is measured to be 4.3° C., an iodine value of the plant squalane composition is 2.3 g/100 g, a saponification value of the plant squalane composition is 2 mg KOH/g, an acid value of the plant squalane composition is 0.2 mg KOH/g, and a refractive index of the plant squalane composition is 1.460 (20° C.).

The embodiment further provides an application of the plant squalane composition. The plant squalane composition is applied in cosmetics.

Embodiment 5

The embodiment provides a preparation method of a plant squalane composition. The preparation method comprises steps 1-3.

The step 1 comprises hydrogenating a plant squalene raw material. Squalene in the plant squalene raw material accounts for 70.0 wt % of a total weight of the plant squalene raw material (remaining components in the plant squalene raw material are plant olefins, a plant wax and a small amount of fatty acid alkyl ester, where the plant olefins and the plant wax have the same boiling point, and the fatty acid alkyl ester have a higher boiling point than the plant olefins and the plant wax). A catalyst for hydrogenating the plant squalene raw material is a 1 wt % metal nickel (product name: Pricat Ni 62/15P, Johnson Mathey). After the plant squalene raw material and the catalyst are evenly mixed, the plant squalene raw material is hydrogenated at a hydrogenation temperature of 210° C. for 6 hours under a hydrogenation pressure of 10 MPa.

During a hydrogenation process, part of the squalene is converted into cyclosqualane. A conversion rate of the squalene is monitored by the GC-MS. A content of the squalane and a content of the cyclosqualane in a crude plant squalane composition obtained after the hydrogenation process are respectively 65.8 wt %, and 4.0 wt %, of a total weight of the crude plant squalane composition. A remaining material is a small amount of non-squalane alkane, wax, alkyl ester, and pigments, etc., and a ratio of the cyclosqualane to the squalane is 6.08%.

The step 2 comprises separating the squalane and impurities in the crude plant squalane composition by fractionation. The step 2 specifically comprises steps 21 and 22.

The step 21 comprises performing a first distillation on the crude plant squalane composition obtained in the step 1. Specifically, the crude plant squalane composition is continuously introduced into a falling film distillation tower with 20 theoretical plates, and the crude plant squalane composition is continuously vaporized in a falling film evaporator of the falling film distillation tower, is balance, and separated in a distillation tower of the falling film distillation tower. The first distillation is carried out under a vacuum of 150 Pa, a bottom temperature of 215° C., and a top temperature of 188° C. As a result, light components are continuously extracted, where the light components comprises non-squalane alkane, a small amount of the squalane and the fatty acid alkyl ester.

The step 22 comprises performing a second distillation. A tower bottom material obtained after a first stage distillation is continuously introduced into the falling film distillation tower with 20 theoretical plates. The tower bottom material is continuously vaporized in the falling film evaporator, and the tower bottom material is allowed to balance and separate in the distillation tower. The second distillation is carried out under the vacuum of 80 Pa, the bottom temperature of 230° C., and the top temperature of 190° C. A main component containing the squalane is continuously extracted. The content of squalane in the main composition is detected to be 92.1 wt %, and the content of cyclosqualane is 2.0 wt %.

The step 3 comprises refining the plant squalane composition. A refining process comprises winterization, decolorization and deodorization.

A melting point of the plant squalane composition finally obtained is measured to be 2.4° C., an iodine value of the plant squalane composition is 1.9 g/100 g, a saponification value of the plant squalane composition is 2.9 mg KOH/g, an acid value of the plant squalane composition is 0.2 mg KOH/g, and a refractive index of the plant squalane composition is 1.450 (20° C.).

The embodiment further provides an application of the plant squalane composition. The plant squalane composition is applied in cosmetics.

Embodiment 6

The embodiment provides a preparation method of a plant squalane composition. The preparation method comprises steps 1-3.

The step 1 comprises hydrogenating a plant squalene raw material. Squalene in the plant squalene raw material accounts for 89.5 wt % of a total weight of the plant squalene raw material (remaining components in the plant squalene raw material are plant olefins, a plant wax, and a small amount of fatty acid alkyl ester, where the plant olefins and the plant wax have the same boiling point, and the fatty acid alkyl ester have a higher boiling point than the plant olefins and the plant wax). A catalyst for hydrogenating the plant squalene raw material is a 2 wt % nickel-based catalyst (product name: Nysosel, Engelhard Corporation). After the plant squalene raw material and the catalyst are evenly mixed, the plant squalene raw material is hydrogenated at a hydrogenation temperature of 190° C. for 7 hours under a hydrogenation pressure of 15 MPa.

During a hydrogenation process, part of the squalene is converted into cyclosqualane. A conversion rate of the squalene is monitored by the GC-MS. A content of the squalane and a content of the cyclosqualane in a crude plant squalane composition obtained after the hydrogenation process are respectively 84.0 wt %, and 2.5 wt %, of a total weight of the crude plant squalane composition. A remaining material is a small amount of non-squalane alkane, wax, alkyl ester, and pigments, etc., and a ratio of the cyclosqualane to the squalane is 2.98%.

The step 2 comprises separating the squalane and impurities in the crude plant squalane composition by fractionation. The step 2 specifically comprises steps 21 and 22.

The step 21 comprises performing a first distillation on the crude plant squalane composition obtained in the step 1. Specifically, the crude plant squalane composition is continuously introduced into a falling film distillation tower with 20 theoretical plates, and the crude plant squalane composition is continuously vaporized in a falling film evaporator of the falling film distillation tower, is balance, and separated in a distillation tower of the falling film distillation tower. The first distillation is carried out under a vacuum of 80 Pa, a bottom temperature of 210° C., and a top temperature of 175° C. As a result, light components are continuously extracted, where the light components comprises non-squalane alkane, a small amount of the squalane and the fatty acid alkyl ester.

The step 22 comprises performing a second distillation. A tower bottom material obtained after a first stage distillation is continuously introduced into the falling film distillation tower with 20 theoretical plates. The tower bottom material is continuously vaporized in the falling film evaporator, and the tower bottom material is allowed to balance and separate in the distillation tower. The second distillation is carried out under the vacuum of 150 Pa, the bottom temperature of 235° C., and the top temperature of 192° C. A main component containing the squalane is continuously extracted. The content of squalane in the main composition is detected to be 94.5 wt %, and the content of cyclosqualane is 1.0 wt %.

The step 3 comprises refining the plant squalane composition. A refining process comprises winterization, decolorization and deodorization.

A melting point of the plant squalane composition finally obtained is measured to be 5° C., an iodine value of the plant squalane composition is 2.4 g/100 g, a saponification value of the plant squalane composition is 1.7 mg KOH/g, an acid value of the plant squalane composition is 0.1 mg KOH/g, and a refractive index of the plant squalane composition is 1.460 (20° C.).

The embodiment further provides an application of the plant squalane composition. The plant squalane composition is applied in cosmetics.

Table 1 is a comparison table of results of the Embodiments 1-6.

| Embodiment | Squalene content in raw material | Content of squalane in crude plant squalane composition | Content of cyclosqualane in crude plant squalane composition | Ratio of cyclosqualane to squalane | Content of squalane in the plant squalane composition finally obtained | Content of cyclosqualane in the plant squalane composition finally obtained |
|---|---|---|---|---|---|---|
| 1 | 76.3% | 71.0 wt % | 4.5 wt % | 6.34% | 93.5 wt % | 1.8 wt % |
| 2 | 73.5% | 71.3 wt % | 2.2 wt % | 3.09% | 93.8 wt % | 1.2 wt % |
| 3 | 91.0% | 90.0 wt % | 0.9 wt % | 1.00% | 96.8 wt % | 0.5 wt % |
| 4 | 85.2% | 75.6 wt % | 7.5 wt % | 9.92% | 92.0 wt % | 3.0 wt % |
| 5 | 70.0% | 65.8 wt % | 4.0 wt % | 6.08% | 92.1 wt % | 2.0 wt % |
| 6 | 89.5% | 84.0 wt % | 2.5 wt % | 2.98% | 94.5 wt % | 1.0 wt % |

In the plant squalane composition and the preparation method of the present disclosure, the plant squalene raw material with the squalene of the content not less than 70.0 wt % is hydrogenated and refined. In the hydrogenation process, although the cyclosqualane is produced by side reactions during the hydrogenation process, the present disclosure is able to partially remove the cyclosqualane by high vacuum distillation during the refining process, reduce the proportion of the cyclosqualane in the plant squalane composition, further enrich the squalane, and maintain the content of the cyclosqualane at 0.5-3.0 wt %, and improve the content and quality of the squalane. In addition, only a cheap nickel-based catalyst (i.e., the metallic nickel, the supported nickel, or the Raney nickel) is needed in the hydrogenation process, and no organic solvent needs to be added, which is environmentally friendly. Moreover, the cheap nickel-based catalyst is a disposable catalyst, and there is no need to consider reuse of the catalyst, which greatly reduces a difficulty of the hydrogenation of the squalene and improves stability of hydrogenation. The above-mentioned embodiments only represent some embodiments of the present disclosure. The descriptions thereof are specific and detailed, but should not be construed as a limitation of the scope of the present disclosure. It should be pointed out that for those of ordinary skill in the art, without departing from the concept of the present disclosure, modifications and improvements can be made. The modifications and the improvements belong to the protection scope of the present disclosure. Therefore, the protection scope of the present disclosure should be subject to the attached claims.

What is claimed is:

1. A preparation method of a plant squalane composition, wherein the plant squalane composition comprising:
   at least 92.0 wt % of squalane by weight; and
   0.5-3.0 wt % of cyclosqualane by weight;
   wherein a chemical structure of the squalane is:

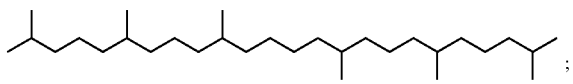 [SMILES: CC(C)CCCC(C)CCCC(C)CCCCC(C)CCCC(C)CCCC(C)C]

wherein a chemical structure of the cyclosqualane is:

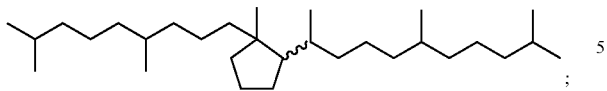

wherein the preparation method comprising:
  a step 1: hydrogenating a plant squalene raw material, wherein squalene in the plant squalene raw material accounts for at least 70.0 wt % of a total weight of the plant squalene raw material;
  a step 2: separating the squalane and impurities by fractionation to obtain the plant squalane composition, wherein a content of the squalane in the plant squalane composition is not less than 92.0 wt %, and a content of the cyclosqualane in the plant squalane composition is 0.5-3.0 wt %; and
  a step 3: refining the plant squalane composition;
  wherein the step 2 comprises:
    a step 21, performing a first distillation to remove plant alkane, fatty acid alkyl ester, and a small amount of the squalane, wherein removed plant alkane and removed fatty acid alkyl este have a low boiling-point, and first remaining material comprises most of the squalane, plant alkane, the cyclosqualane, and plant asphalt; and
    a step 22: performing a second distillation to obtain a main composition containing the squalane and the cyclosqualane, and enabling that the content of the squalane in the main composition is not less than 92.0 wt % and the content of the cyclosqualane is 0.5-3.0 wt % by adjusting parameters, wherein second remaining material is the plant asphalt with a high-boiling point;
  wherein in the step 1, a catalyst for hydrogenating the plant squalene raw material is metal nickel, supported nickel, or Raney nickel, a hydrogenation temperature is 180-220° C., and a hydrogenation pressure is 5-15 MPa, and a hydrogenation time is 6-24 hours;
  and wherein during the step 1 hydrogenating, part of the squalene is converted into the cyclosqualane, a ratio of the cyclosqualane to the squalane is 1-10%.

2. The preparation method of the plant squalane composition according to claim 1, wherein the first distillation is carried out on a packed tower equivalent to 20 theoretical plates, under a system vacuum of 10-1000 Pa, with a bottom temperature of 200-230° C. and a top temperature of 170-190° C.

3. The preparation method of the plant squalane composition according to claim 1, wherein the second distillation is carried out on a packed tower equivalent to 20 theoretical plates, under a system vacuum of 10-1000 Pa, with a bottom temperature of 220-250° C. and a top temperature of 180-200° C.

4. The preparation method of the plant squalane composition according to claim 1, wherein in the step 3, a refining process comprises winterization, decolorization and deodorization, and a melting point of the plant squalane composition after the refining process is 0-5° C.

* * * * *